United States Patent [19]
Chong

[11] Patent Number: 5,695,988
[45] Date of Patent: Dec. 9, 1997

[54] CULTURE DEVICE FOR SAMPLING AND/OR COUNTING MICRO-ORGANISM

[76] Inventor: Sue Kheng Chong, 27 Jalan Limau Kasturi, Bangsar Park, 59000 Kuala Lumpur, Malaysia

[21] Appl. No.: 341,566

[22] PCT Filed: May 24, 1993

[86] PCT No.: PCT/GB93/01063

§ 371 Date: Mar. 21, 1995

§ 102(e) Date: Mar. 21, 1995

[87] PCT Pub. No.: WO93/24608

PCT Pub. Date: Dec. 9, 1993

[30] Foreign Application Priority Data

May 22, 1992 [GB] United Kingdom ............... 9210983
Mar. 19, 1993 [GB] United Kingdom ............... 9305665

[51] Int. Cl.$^6$ .................................................. C12M 3/00
[52] U.S. Cl. ............................ 435/305.1; 435/309.2; 435/309.4
[58] Field of Search .................... 435/309.2, 309.4, 435/305.1

[56] References Cited

U.S. PATENT DOCUMENTS

| | | | |
|---|---|---|---|
| 3,203,870 | 8/1965 | Andelin | 435/309.4 |
| 3,751,341 | 8/1973 | Seitz et al. | 435/309.4 |
| 3,881,993 | 5/1975 | Freake | 435/309.4 |
| 3,902,972 | 9/1975 | Beckford | 195/139 |
| 4,250,256 | 2/1981 | Weilinger et al. | 435/309.4 |
| 4,598,050 | 7/1986 | Brown | 435/309.4 |
| 4,634,676 | 1/1987 | Sapatino | 435/309.4 |
| 4,717,667 | 1/1988 | Provonchee | 435/309.4 |

FOREIGN PATENT DOCUMENTS 0 267 093 A1  10/1987  European Pat. Off.
25 41 000 B1  11/1976  Germany.

*Primary Examiner*—David A. Redding
*Attorney, Agent, or Firm*—Larson & Taylor

[57] ABSTRACT

A culture device is described comprising a solid body of culture medium and supporting means for maintaining the integrity of the body of culture medium, the culture medium providing a culture surface having an endless boundary or perimeter, a body of medium protruding from and the culture surface being spaced from any aforesaid means disposed externally of the body of culture medium.

22 Claims, 2 Drawing Sheets

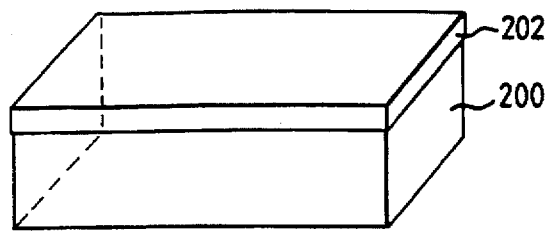
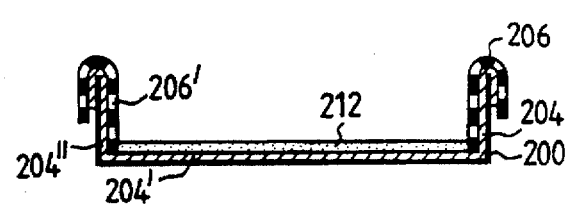
FIG.6  FIG.8
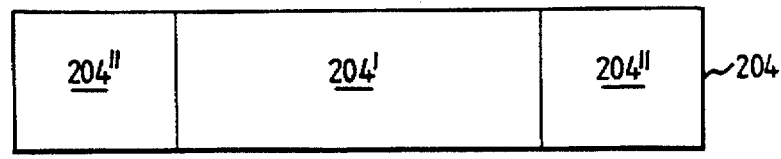
FIG.7
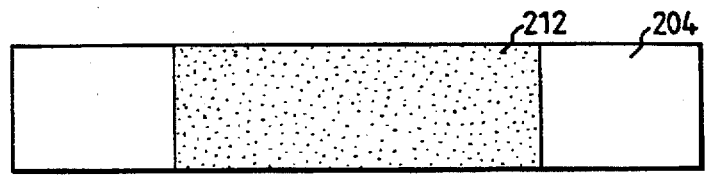
FIG.9
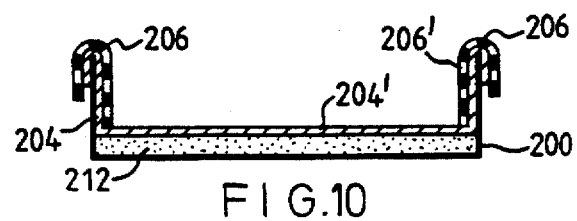
FIG.10
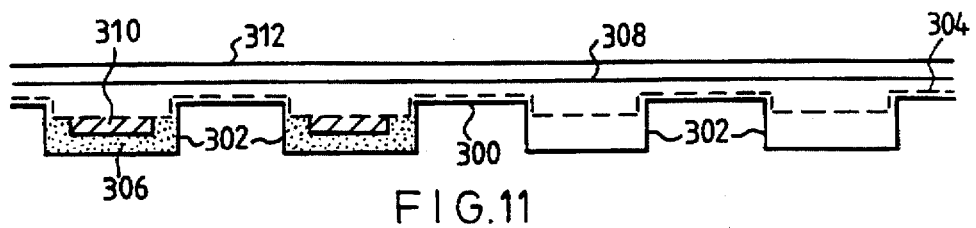
FIG.11
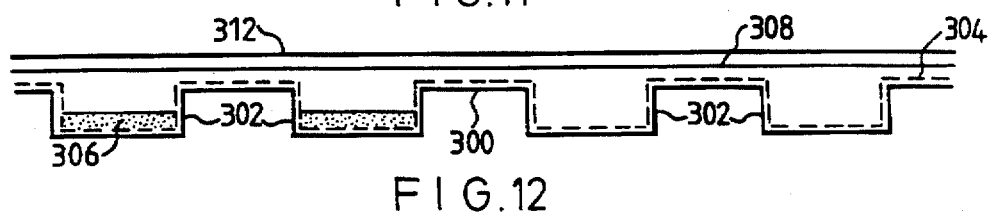
FIG.12

CULTURE DEVICE FOR SAMPLING AND/ OR COUNTING MICRO-ORGANISM

The present invention relates to a culture device for sampling micro-organisms and/or counting micro-organisms. The present invention also relates to apparatus by means of which Such a culture device can be prepared.

Microbial count tests have become a useful sanitary control tool for monitoring sanitation and quality levels of food plants to ensure that products are safe and wholesome. The tests involve transfer of micro-organisms from cleaned and sanitised test surfaces onto a culture agar medium (CAM) which allows growth of a wide range of micro-organisms. After a period of incubation, each microbial cell develops into a visible colony of cells. The number of colonies provides a measure of the number of micro-organisms on the test surface.

Various methods are available for assessment of microbiological status of food contact surfaces in equipment such as piping, containers, tables and conveyors which are in contact with food products. Of these methods, the rinsing, swabbing and agar contact methods have been considered as satisfactory and have gained general acceptance.

In the agar contact method a replicate organism direct agar contact (RODAC) plate is used. The RODAC plate provides a simple agar contact tool for sampling surfaces. It is useful for monitoring the sanitary quality of surfaces used in food industries and hospitals. The RODAC plate is best suited for flat smooth impervious surfaces such as ceiling, wall and floor surfaces and surfaces of tables, containers and conveyors.

The RODAC plate has a rim and is filled with CAM which has a slightly convex surface with the centre of its meniscus rising above the rim. The surface of the CAM is pressed against the test surface to be sampled. It is necessary to make good contact of the agar with the test surface. Accordingly when sampling, care has to be taken to ensure that the entire agar meniscus contacts the test surface: a rolling uniform pressure on the back of the plate to effect contact aids in achieving this.

A disadvantage inherent in the rinsing, swabbing and agar contact methods is that uniformity and consistency in sampling depend primarily on the skill of persons taking the samples. Technicians need to be trained in sampling technique in order to obtain uniform and meaningful results.

In particular in the agar contact method the filling of the RODAC plate with CAM to achieve a slightly convex surface is a slow, cares and exacting process. Additionally it is not sufficient simply to press the CAM of the filled plate against the test surface since only that part of the surface of the CAM within the curved edge portion of the meniscus would contact the test surface. This part of the surface is of indefinite area. Thus the area of the test surface contacted would be indefinite and consequently an accurate account of microorganisms per unit area of the test surface would not be obtainable.

The present invention enables the above-mentioned disadvantage to be overcome and provides, at least in preferred embodiments, additional advantages.

In accordance with a first aspect of the invention, there is provided a culture device comprising a body of culture medium and supporting means for maintaining the integrity of the body of culture medium, the culture medium providing a surface (referred to below as the "the culturing surface") having a defined endless boundary or perimeter, the body of culture medium protruding from and the culturing surface being spaced from any aforesaid means disposed externally of the body of culture medium.

The endless boundary or perimeter is defined by a side surface on contiguous side surfaces of the culture medium, which side surface or surfaces meet the culturing surface, preferably abruptly, along an endless line or endless series of lines at an angle substantially differing from 180°, preferably at an angle of 90°, so that the boundary or perimeter is precisely defined.

The defined boundary or perimeter of the culturing surface enables its surface area to be clearly ascertained. This enables the number of micro-organisms per unit area on a test surface and which have been transferred to the culturing surface to be accurately evaluated.

The supporting means may be at least partly external to the body of culture medium and/or may be at least partly internal to the body of culture medium.

Thus the supporting means may be wholly external to the body of culture medium, wholly internal of the body of culture medium or may be in part external to and in part internal of the body of culture medium.

The supporting means may comprise an open cell sponge or foam or material having a three-dimensional reticulated structure, such as a skeletal foam, or other pervious or permeable material impregnated with the culture medium. A suitable material is like that used in household scouring sponges. Other suitable materials include pervious or permeable flexible and preferably soft sheet materials such as woven and non-woven fabric and wet-strength paper.

Materials as described in the preceding paragraph allow liquid culture medium to infiltrate and impregnate their voids and interstices and they provide good support and anchorage for the culture medium when it has solidified.

The supporting means may comprise a base external to the body of culture medium.

When the supporting means is in part external and in part internal to the body of culture medium, the part internal to the body of culture medium constitutes an anchor to hold the culture medium on the part of the supporting means external to the culture medium, which latter part may constitute a base.

Preferably the anchor is held fast or otherwise attached to the base.

Preferably the culturing surface is spaced from a peripheral portion of the base by e.g. 1 to 5 mm.

The culturing surface may be circular, rectangular or square.

The culture medium may comprise agar.

The culturing surface may be flat. This enables the culture device to be applied directly to a flat test area to achieve full contact with the test area without manipulation of the culture device.

Alternatively the culturing surface may be convex or concave for application to particular shapes of test surface.

The anchor may be a disc or plate preferably perforate or in the form of a grid. It may alternatively consist of a flexible porous or pervious absorbent material such as described above in respect of the supporting means.

The base may be in the form of a container, the peripheral portion of the base being a rim of the container.

The term "rim" in relation to the container is intended to encompass any endless free edge or extremity of the container, which free edge or extremity can surround and define the extent of the body of the culture medium.

When the base is in the form of a container, the anchor may be a snap fit on a projection upstanding from centre of the container or may be connected to or integral with a member which is friction fit in the container. Such an anchor is preferably level with the rim of the base.

It may be particularly advantageous for the base to comprise a soft flexible or pliable sheet and for the anchor, if present, also to be flexible or pliable. This enables the body of culture medium to be deformed so that the culture surface can conform to the shape of a test surface to which it is applied.

In accordance with the invention there is further provided an apparatus for preparing a culture device, comprising a base for holding a body of culture medium, and a cover which can cooperate with the base to define, together with the base, a cavity for shaping a body of culture medium, the cavity having a surface provided by the cover for forming the culturing surface of the culture medium, said surface of the cavity being spaced from a peripheral portion of the base when the cover cooperates with the base and having a defined endless boundary or perimeter so that the body of culture medium shaped in the cavity has a corresponding defined endless boundary or perimeter spaced from the peripheral portion of the base.

The surface of the cavity may comprise an internal surface of the cover.

The base may be in the form of a container, the peripheral portion of the base being a rim of the container.

The cover may include means to space said surface of the cavity from the rim of the base by a desired distance when the cover is fitted onto the base.

Said means may comprise a shoulder or abutment of the cover, which shoulder or abutment is engagable with the rim of the base.

The base may be as described above with reference to the supporting means.

The apparatus may include an anchor such as described above, to be embedded in the culture medium.

In accordance with a second, preferred aspect of the invention there is provided a culture device comprising a strip of fabric (or other flexible pervious or permeable material), a central portion of which is impregnated by and supports a body of culture medium providing a culturing surface spaced from the strip and having a defined endless boundary or perimeter, end portions of the strip, for use in manipulating the device, being free of the culture medium.

In accordance with the invention there is further provided apparatus for preparing a culture device, comprising a container and a flexible sheet element having at least a central portion which is porous, permeable or pervious, first means providing a cavity in a container for receiving the central portion of the sheet element and for shaping a body of culture medium formed by solidification or setting of liquid culture medium, the culture medium when liquid impregnating the central portion of the sheet element whereby the body of the culture medium and the sheet element form a culture device, the central portion supporting the culture medium and maintaining the integrity thereof when the culture medium is solidified, the body of culture medium having a culturing surface and the cavity defining side surfaces of said body, which side surfaces meet the culturing surface to provide a defined endless boundary or perimeter of the culturing surface, and second means to maintain the central portion of the sheet element taut in the cavity and for allowing end portions of the sheet element to be kept free of the culture medium when the culture medium is solidifying or setting.

Preferably the container has a base which constitutes the base of the cavity.

Preferably side walls of the container form side walls of the cavity.

Preferably the second means not only holds the central portion of the sheet element taut but also forms side walls of the cavity.

There is further provided a method of preparing a culture device comprising providing a container and a flexible sheet element having at least a central portion which is permeable or pervious, locating the central portion of the sheet element in a cavity defined in the container with end portions of the sheet element external to the cavity, introducing liquid culture medium into the cavity to impregnate the central portion of the sheet element, and, while maintaining end portions of the sheet element free of the culture medium and maintaining the central portion of the sheet element taut, allowing or causing the culture medium to solidify to form a body of culture medium having a free upper culturing surface or a culturing surface defined by a base of the cavity and the cavity defining side surfaces of said body which side surfaces meet the culturing surface to provide a defined endless boundary or perimeter of the culturing surface.

Preferably the sheet element is of woven or non-woven fabric.

Preferably the cavity is defined by side walls and a base of the container and by means which hold the central portion of the sheet element taut.

Another culture device according to the invention comprises a sheet member defining a plurality of cavities and a sheet of fabric or other pervious material extending over the sheet and into the cavities, the body of culture medium filling at least the bottom portion of each cavity and impregnating the pervious material, whereby the pervious material in each cavity forms an anchor for the body of culture medium, the base of each cavity defining a culturing surface of the culture medium, the culturing surface having a defined endless boundary or perimeter.

The invention is further described below by way of example with reference to the accompanying drawings, wherein:

BRIEF DESCRIPTION OF THE DRAWINGS

FIG. 6 is a perspective view of a container and a lid of a further apparatus according to the invention;

FIG. 7 is a plan view of a fabric strip of the apparatus of FIG. 6;

FIG. 8 is a sectional view along a vertical plane of the apparatus of FIG. 6, culture medium having been added to the apparatus to prepare a culture device according to the invention;

FIG. 9 is a vertical plan view of the culture device of FIG. 8 or FIG. 10,

FIG. 10 is similar to FIG. 8 but shows a modification of the apparatus;

FIG. 11 shows another embodiment of the invention; and

FIG. 12 shows a modification of the embodiment of FIG. 11.

Figure 1:
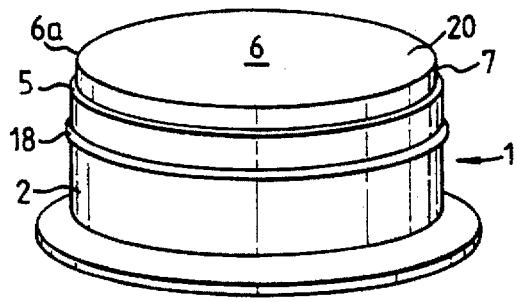
FIG. 1 is a perspective view of a culture device according to the invention.
Figure 2:
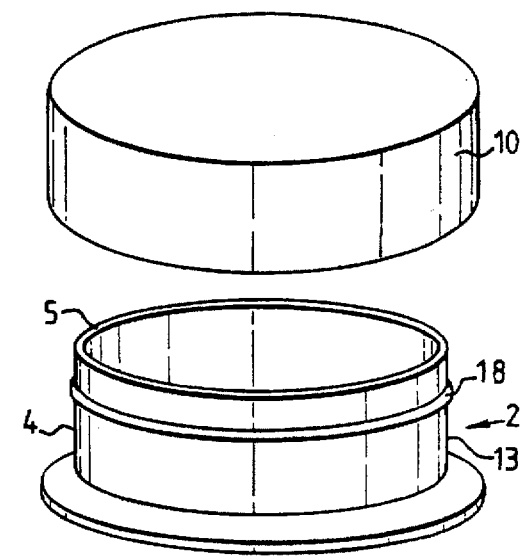
FIG. 2 is a perspective view of apparatus according to the invention for preparing the culture device of FIG. 1.
Figure 3:
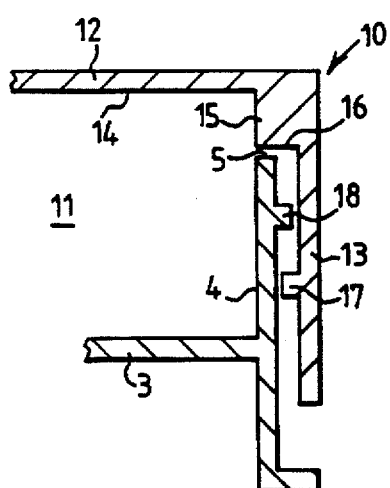
FIG. 3 is a vertical sectional view of part of the side walls of the apparatus of FIG. 2.

Referring to the drawings there is shown a circular culture device 1 comprising a base or container 2 which holds a body of culture medium 20. The base 2 has a bottom wall 3 and a side wall 4. The side wall 4 has a rim 5. The culture medium 20 protrudes from the base 2 and has a smooth, flat surface 6 ("the culturing surface") raised above the rim 5 by a distance of 2 mm.

A side surface 7 of the culture medium 20 extends upwardly from the rim 5 of the base 2 to the culturing surface 6. The culturing surface 6 and the side surface 7 meet at an angle of 90° to provide a precisely defined endless boundary or perimeter 6a of the culturing surface. This defined perimeter enables the surface area of the culturing surface 6 to be precisely determined.

The internal diameter of the base 2 is selected to provide a predetermined surface area of the culturing surface 6.

Figure 4:
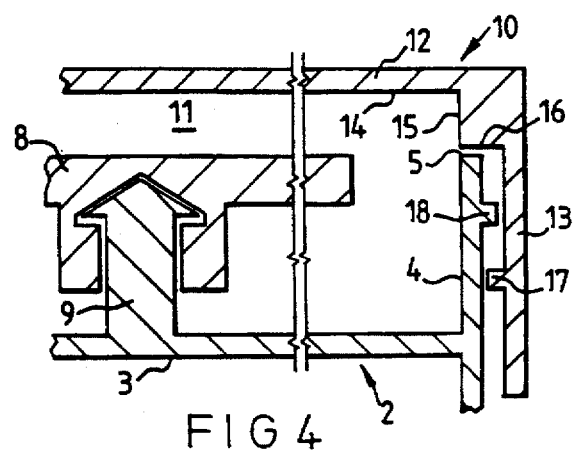
FIG. 4 is a vertical sectional view of part of the apparatus of FIG. 2 showing an anchor.

The base 2 may be provided, as shown in FIG. 4, with an anchor comprising a thin disc 8 which is on the same horizontal plane as the rim 5 of the base 2. The disc 8 is a snap fit on a post 9. The post 9 is integrally formed with the base 2 and projects upwardly from the bottom wall 3 of the base. The diameter of the disc 8 is less than the internal diameter of the base 2. The disc 8 is preferably perforate. The disc 8 serves to hold and support the culturing medium.

Figure 5A:
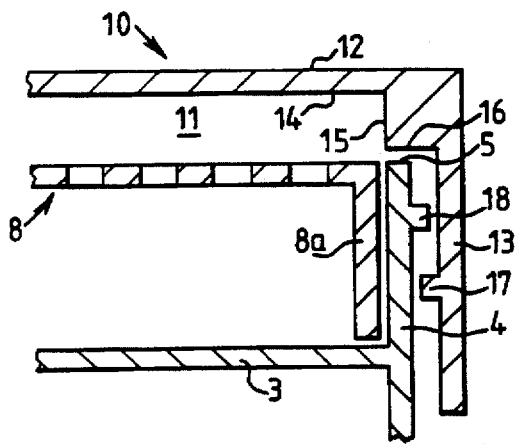
FIG. 5A is similar to FIG. 4 but shows an alternative anchor.

FIG. 5A shows an alternative anchor. The anchor comprises a perforate disc 8 integrally formed with a depending peripheral side wall or skirt 8A which can fit within the base 2 and frictionally engage the side wall 4 of the base. (FIG. 5 shows a space between the side walls 4 and 8A merely for clarity of illustration).

The culture device 1 further includes a lid or cover 10 which is a close fit onto the base part 2 to define, together with the base part 2, a cavity 11. The cover 10, although close fitting on the base 2, is not tight fitting and accordingly can be readily slipped onto the base 2 and easily removed.

The cover 10 has a top wall 12 and a side wall 13. These walls provide respectively an internal flat smooth top surface 14 and a cylindrical internal side surface 15. These surfaces meet at an angle of 90°.

The side wall 13 of the cover 10 is provided with an abutment or shoulder 16.

The side wall 13 of the cover 10 has an internal lip 17 below the abutment or shoulder 16. The lip 17 can cooperate with a corresponding external lip 18 on the side wall 4 of the base 2.

The cover 10 can be fitted into the base 2 with the shoulder 16 resting on the rim 5 so that the base is fully closed and the surface 14 of the cover is separated from the rim 5 of the base 2 by a desired distance (preferably about 2 mm). Alternatively the cover 10 can be fitted onto the base 2 with the lip 17 resting on the lip 18 so that shoulder 16 is held above the rim 5.

In order to prepare the culture device 1, a culture medium in liquid form, e.g. melted agar, is introduced into the cover 10. This can be carried out by inverting the cover 10 and pouring the culture medium directly into the cover and then fitting the base 2 onto the cover or by pouring the culture medium into the base 2 and then fitting the cover onto the base and inverting the base 2 and the cover 10 together to transfer the culture medium into the cover. The culture medium is then allowed to cool thereby to set or solidify to form the body 20 of culture medium. The amount of culture medium must be such as to more than fill the cavity 11 from the surface 14 of the cover 10 to the rim 5 of the base 2. If the base 2 is provided with the anchor 8, then the anchor becomes embedded in the solidified culture medium and holds the culture medium firmly in place. The surface 14 of the cover shapes the culturing surface 6 of the culture medium as the culture medium solidifies. Similarly the surface 15 of the cover shapes the side surface 7 of the culture medium.

The cover 10 can be removed for inspection of the solidified culture medium or for use of the culture device. Preferably the cover 10 is kept on the base 2 until the culture device 1 is to be used in order to protect the culture medium from contamination. If desired the cover 10 can be replaced on the base 2 without touching the surface of the culture medium by resting the lip 17 on the lip 18.

In use of the culture device i, the cover 10 is removed and the culturing surface 6 is pressed directly against a test surface to transfer micro-organisms to the culturing surface 6 from the test surface. The surface 6 is then removed from the test surface and the micro-organisms transferred to the surface 6 are allowed to multiply into visible colonies. The number of colonies corresponds to the number of micro-organisms transferred from the test surface to the surface 6. Since the area of the surface 6 is precisely determinable, the number of micro-organisms transferred from the test surface to the surface 6 per unit area of the test surface can be precisely determined.

The culture device 1 may be round (as shown) or square in plan. It is preferred that the base 2 and the cover 10 are round for convenience, versatility and ease of manipulation. The base part 2 and the cover 10 may be made of clear transparent material, such as polystyrene, which lends itself to fabrication and can withstand sterilizing temperatures or gamma radiation.

Figure 5B:
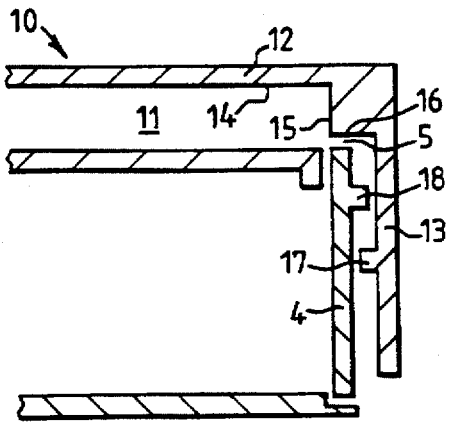
FIG. 5B is similar to FIGS. 4 and 5A but shows another alternative anchor.

The perforated disc or plate 8 forming the anchor in FIG. 5A may be replaced, as shown in FIG. 5B, by porous or pervious material such as open cell sponge or foam or a reticulated structure, such as that used in household scouring sponges. The anchor 8 may be covered by fabric, towelling, or wet strength paper secured to the anchor. Alternatively the anchor itself could be made of fabric or wet strength paper, towelling, sponge or other materials as discussed above.

Reference is now made to FIGS. 6 to 10.

Apparatus for preparing a culture device comprises a rectangular parallel-pipedal open-topper container 200, a lid or cover 202 for the container and a strip 204 of woven or non-woven fabric.

The width of the strip matches the internal width of the container 200. The length of the strip is somewhat greater than the total of the internal length of the container plus twice the internal height of the container. Spring clips 206, as shown in FIG. 8, may be provided to hold the strip 204 in the container 200 with a central portion 204' of the strip held taut between the ends of the container and in contact with the base of the container and with end portions 204" of the strip extending over end walls of the container.

The clips 206 have limbs 206' which are sufficiently long to press the central portion 204' of the strip 204 into close contact with the base of the container 200.

In use of the apparatus the strip 204 is arranged as shown in FIG. 8, the strip being held taut between the clips 206 and pressed against the base of the container 200. Then liquid culture medium is poured into the container. The culture medium is spread out over the fabric strip in a layer 212 and solidifies to form a body of culture medium 212 supported by and impregnating the fabric.

The upper horizontal surface of the solidified body 212 of culture medium constitutes a culturing surface. The side walls of the container 200 and the limbs 206' of the clips 206 define side surfaces of the body of culture medium and the side walls of the container 200 also define side surfaces of the body 212 of culture medium. These side surfaces meet the culture surface at 90° and thus the culturing surface has a defined endless boundary or perimeter.

A lid 202 may be placed on the container 200 to protect the body 212 of culture medium from contamination.

The fabric strip with the solidified body 212 of culture medium constitutes a culture device. In use of the culture device the device is removed from the container and manipulated by means of the end portions 204" of the fabric strip.

The culture device may be used in like manner to the culture device described above. After application of the culturing surface to a test surface the culture device may be replaced in the container 200 to allow incubation of microorganisms on the culturing surface. The lid 202 may be used to prevent contamination of the culturing surface during incubation of the microorganisms.

It will be appreciated that because the fabric strip 204 is flexible the device can be used in conjunction with test surfaces which may be flat, curved or uneven, the body of culture medium and the fabric strip accommodating themselves to the shapes of such test surfaces.

The strip 204 may be of wet strength paper instead of woven or non-wove fabric.

The strip 204 may be temporarily stuck to the end walls and base of the container 200 by adhesive thereby obviating the use of the clips 206.

FIG. 10 shows a modification of the apparatus shown in FIG. 8.

Referring to FIG. 10, the limbs 206' of the clips 206 are shorter so that the central portion 204' of the strip 204 when held taut between the ends of the container 200 is spaced from the base of the container. The culture medium when set impregnates the central portion 204' of the strip 204 but has a layer between the strip and the base of the container. The lower surface of the set culture medium constitutes a culturing surface, which is smoother than the culturing surface provided by use of the apparatus shown in FIG. 8.

FIG. 11 shows a further embodiment of the invention.

Referring to FIG. 11, a sheet 300 of clear transparent plastic (e.g. polystyrene) is formed to provide a plurality of blisters or cavities 302, each having a cylindrical side wall which meets the base of the cavity at 90°. A piece of fabric 304 is laid over the plastic so as to hang into each cavity. The fabric 304 hanging into the cavity may have a piece of sponge attached to it. A piece of sponge 310 is shown in cavity 302 in FIG. 11. The culture medium is then poured over the fabric and penetrates through the fabric to fill each cavity. The culture medium is allowed to set. The resulting solidified body 306 of culture medium in each cavity forms a culture device, the culture medium impregnating the fabric/sponge which forms an anchor for the medium. A sheet of aluminium foil 308 may be laid over the fabric to shield the culture devices from contamination. A suitable plastic sheet 312 may be added to protect the aluminium foil.

It will be appreciated that the base of each cavity defines a culturing surface of the body of culture medium, the culture surface having a defined endless boundary or perimeter.

FIG. 12 shows a modification of the embodiment of FIG. 11. As shown in FIG. 12, the piece of fabric 304 extends down the sides of each cavity and across each cavity, adjacent/along its base. The upper horizontal surface of the solidified body of culture medium constitutes the culturing surface.

Each culture device may be individually removed from its cavity for use when required.

It will be further appreciated that the aluminium foil may be firmly adhered to the fabric and solidified culture medium to provide an assembly in which the culture devices are hermetically sealed. The assembly may be provided with perforations between the culture devices so that the portions of the assembly, each containing one culture device, can be readily separated from the remainder of the assembly. When the aluminium foil is removed from such a separated portion of the assembly, the aluminium foil can then be removed from that portion and the culture device lifted out of the cavity. After completion of sampling the culture device can be placed with the culture surface upward on the separated portion of the plastic sheet. The separated portion of the cavity is used to cover the culture device and the two parts are stapled together for incubation.

The cavity 302 may be round, as shown, or square or rectangular.

I claim:

1. A culture device comprising a solid body of culture medium and supporting means for maintaining the integrity of the body of culture medium, the culture medium providing a culturing surface having an endless boundary or perimeter, the body of culture medium protruding from and the culturing surface being spaced from any aforesaid means disposed externally of the body of culture medium, the endless boundary or perimeter being defined by a side surface or contiguous side surfaces of the culture medium, which side surface or surfaces meet the culturing surface abruptly along an endless line or endless series of lines at an angle substantially differing from 180° so that the boundary or perimeter is defined, the supporting means being partly internal of and partly external to the body of culture medium.

2. A culture device according to claim 1, wherein the supporting means at least in part is flexible or pliable to allow the culture medium to deform to accommodate to the shape of a test area to which the culture medium is applied.

3. A culture device according to claim 1, wherein the supporting means comprises porous, pervious or permeable material impregnated with the culture medium.

4. A culture device according to claim 3, wherein the porous, pervious or permeable material comprises open cell sponge or foam or material having a three-dimensional reticulated structure.

5. A culture device according to claim 1, wherein the culturing surface is spaced from a peripheral portion of the supporting means external to the culture medium by 1 to 5 mm.

6. A culture device according to claim 3, wherein the disc or plate is perforate or in the form of a grid.

7. A culture device according to claim 1, wherein the supporting means comprises a base external to the body of culture medium and an anchor internal of the body of culture medium and the anchor is held fast or otherwise attached to the base.

8. A culture device according to claim 1, wherein the supporting means comprises a strip of fabric or other flexible porous, pervious or permeable material, a central portion of which is impregnated by and supports the body of culture medium providing the culturing surface spaced from the strip and having the defined endless boundary or perimeter, end portions of the strip, for use in manipulating the device, being free of the culture medium.

9. Apparatus for preparing a culture device, comprising a container and a flexible sheet element having at least a central portion which is porous, permeable or pervious, a cavity, being provided in the container for receiving the central portion of the sheet element and for shaping a body of culture medium formed by solidification or setting of liquid culture medium in the cavity, the culture medium when liquid impregnating the central portion of the sheet element whereby the body of the culture medium and the sheet element form a culture device, the central portion supporting the culture medium and maintaining the integrity thereof when the culture medium is solidified, the body of culture medium having a culturing surface and the cavity defining side surfaces of the body which meet the culturing surface abruptly to define an endless boundary, or perimeter of the culturing surface and removable means for defining side walls of the cavity and for maintaining the central portion of the sheet element taut in the cavity and for allowing end portions of the sheet element to be kept free of the culture medium when the culture medium is solidifying or setting, said means forming walls of the cavity.

10. Apparatus according to claim 9, wherein side walls of the container form side walls of the cavity.

11. A method of preparing a culture device comprising providing a container and a flexible sheet element having at least a central portion which is porous, permeable or pervious, locating the central portion of the sheet element in a cavity defined in the container with end portions of the sheet element external to the cavity, introducing liquid culture medium into the cavity to impregnate the central portion of the sheet element, and, while maintaining end portions of the sheet element free of the culture medium and maintaining the central portion of the sheet element taut, allowing or causing the culture medium to solidify to form a body of culture medium having a free upper culturing surface or a culturing surface defined by a base of the cavity and the cavity defining side surfaces of said body which side surfaces meet the culturing surface to provide a defined endless boundary or perimeter of the culturing surface.

12. A method according to claim 11, wherein the sheet element is of woven or non-woven fabric.

13. A method according to claim 11, wherein the cavity is defined by side walls and a base of the container and by means which hold the central portion of the sheet element taut.

14. A culture device comprising a sheet member defining a plurality of cavities and a sheet of fabric or other pervious material extending over the sheet and into the cavities, the body of culture medium filling at least the bottom portion of each cavity and impregnating the pervious material, whereby the pervious material in each cavity forms an anchor for the body of culture medium, the base of each cavity defining a culturing surface of the culture medium, the culturing surface having a defined endless boundary or perimeter.

15. Apparatus for preparing a culture device, comprising a base for holding a body of culture medium and a cover which can cooperate with the base to define, together with the base, a cavity for shaping a body of culture medium, and supporting means at least partly within the cavity and for maintaining the integrity of the body of culture medium, the cavity having a surface provided by the cover for forming a culturing surface of the body of culture medium, said surface of the cavity being spaced from a peripheral portion of the base when the cover cooperates with the base and having an endless boundary or perimeter, the endless boundary or perimeter being defined by a side surface or contiguous side surfaces of the cavity, which latter surface or surfaces meet the first-mentioned surface of the cavity abruptly along an endless line or series of lines at an angle substantially differing from 180° so that the boundary or perimeter is sharply defined, whereby the body of culture medium shaped in the cavity has an endless boundary or perimeter spaced from the peripheral portion of the base.

16. Apparatus according to claim 15, wherein the supporting means at least in part is flexible or pliable to allow the culture medium to deform to accommodate to the shape of a test area to which the culture medium is applied.

17. A method of preparing a culture device comprising inverting the cover of the apparatus according to claim 15, introducing liquid culture medium into the inverted cover to fill the cover at least up to the level of the peripheral portion of the base when the cover cooperates with the base and then effecting setting or solidification of the culture medium with the base inverted and fitted to the inverted cover.

18. A culture device comprising a solid body of culture medium and supporting means for maintaining the integrity of the body of culture medium, the culture medium providing a culturing surface having an endless boundary or perimeter, the body of culture medium protruding from and the culturing surface being spaced from any aforesaid means disposed externally of the body of culture medium, the endless boundary or perimeter being defined by a side surface or contiguous side surfaces of the culture medium, which side surface or surfaces meet the culturing surface abruptly along an endless line or endless series of lines at an angle substantially differing from 180° so that the boundary or perimeter is defined, the supporting means being at least partly internal of the body of culture medium and comprising woven or non-woven fabric or wet strength paper impregnated with the culture medium.

19. A culture device according to claim 18, wherein the side surface or surfaces meet the culturing surface along an endless line or series of lines at an angle of 90°.

20. A culture device according to claim 18, wherein the supporting means is partly external to the body of culture medium.

21. A culture device according to claim 18, wherein the supporting means comprises a base external to the body of culture medium and an anchor internal of the body of culture medium and the anchor is held fast or otherwise attached to the base.

22. A culture device according to claim 18, wherein the supporting means comprises a strip of fabric or other flexible porous, pervious or permeable material, a central portion of which is impregnated by and supports the body of culture medium providing the culturing surface spaced from the strip and having the defined endless boundary or perimeter, end portions of the strip, for use in manipulating the device, being free of the culture medium.

* * * * *